United States Patent [19]

Inaba et al.

[11] Patent Number: 5,023,383

[45] Date of Patent: Jun. 11, 1991

[54] METHOD FOR PRODUCING AROMATIC ALCOHOL

[75] Inventors: Masashi Inaba; Ryozo Hamana; Hideyuki Hase, all of Yokkaichi; Tatsuro Ashizawa, Kashima, all of Japan

[73] Assignee: Mitsubishi Petrochemical Co., Ltd., Tokyo, Japan

[21] Appl. No.: 460,632

[22] Filed: Jan. 3, 1990

[30] Foreign Application Priority Data

Jan. 13, 1989 [JP] Japan ............................ 1-4862

[51] Int. Cl.$^5$ .................. C07C 27/04; C07C 27/06
[52] U.S. Cl. ......................... 568/815; 568/814
[58] Field of Search ................ 568/814, 815, 385

[56] References Cited

U.S. PATENT DOCUMENTS

| | | | |
|---|---|---|---|
| 4,246,203 | 1/1981 | Wirth ................................. | 568/815 |
| 4,322,567 | 3/1982 | Matsunaga et al. ................ | 568/815 |

FOREIGN PATENT DOCUMENTS

| | | | |
|---|---|---|---|
| 0004036 | 1/1975 | Japan ................................. | 568/814 |
| 0016843 | 1/1984 | Japan ................................. | 568/815 |
| 0110639 | 6/1984 | Japan ................................. | 568/815 |
| 0174737 | 9/1985 | Japan ................................. | 568/815 |

*Primary Examiner*—Werren B. Lone
*Attorney, Agent, or Firm*—Oblon, Spivak, McClelland, Maier & Neustadt

[57] ABSTRACT

Aromatic alcohol is produced by reducing aromatic hydroperoxide with hydrogen in a liquid phase, using a Pt catalyst solely or a catalyst containing Pt and at least one element selected from the group consisting Pb, Sn, Cu, As, Sb, In, Se and Bi in a fixed bed reactor.

15 Claims, No Drawings

METHOD FOR PRODUCING AROMATIC ALCOHOL

BACKGROUND OF THE INVENTION

This invention relates to a process for the production of aromatic alcohols using improved catalysts.

Aromatic alcohols are useful as intermediates for various types of organic compounds and as solvents, and are advantageously produced industrially by the reduction of aromatic hydroperoxides.

Japanese Patent Publication No.26961/1964 and U.S. Pat. No.2,491,926 disclose methods of producing α-cumyl alcohol by reducing cumene hydroperoxide or dicumyl peroxide dissolved in cumene with hydrogen in the presence of hydrogenation catalysts such as Pd, Ni, etc. Such reactions are accompanied by the evolution of heat; therefore, use of a solvent is recommended for mitigating reaction heat and for lowering side reactions as much as possible. As said solvents, water-immiscible solvents such as hydrocarbons are employed. However, deactivation of the catalyst is recognized to occur unexpectedly soon when said solvents are used, so, a method of employing a lower aliphatic alcohol is disclosed by Japanese Patent Laid-open No. 69527/1980. Further, in order to obtain aromatic alcohols in good yield a method is disclosed in Japanese Patent Laid open No.174737/1985, wherein said reduction is conducted in coexistence with amines or some compounds capable of being converted to amines during said hydrogenation reaction.

However, in the hydrogenation method described in said Patent Laid-open, a complex process is necessary for the separation of desired aromatic alcohols from aliphatic alcohols, amines, etc. having different properties from those of the aromatic alcohols. In addition, a complex structure of equipment is needed for the separation of the produced alcohols and a suspended catalyst, and therefore, the method mentioned above can not be advantageously employed for industrial mass production thereof.

Japanese Patent Laid-Open No.16843/1984 discloses, when reducing aromatic hydroperoxide with hydrogen gas in the presence of a catalyst containing Pd, a method wherein a feed liquid containing aromatic hydroperoxide is allowed to pass downstream in a fixed bed reactor. Japanese Patent Laid-open No. 110639/1984 discloses, when reducing aromatic hydroperoxide with hydrogen, a method wherein a Pd catalyst with Pd surface area of at least 200m$^2$/g Pd is employed in the form of a fixed bed.

It is described that in the hydrogenation method in said patent Laid-open elution of the Pd was barely found, and that the desired aromatic alcohols can be rather effectively obtained. The operating time reported in said patent Laid-open was only 720 hours (30 days), whereas, the present inventors conducted an even longer time of operation to find a completely deactivated catalyst at the 70th day of operation (refer to COMPARATIVE EXAMPLE 2 below). In addition, when we measured the concentrations of Pd in the liquid produced by passing aromatic hydroperoxide solutions having concentrations changed over the Pd catalyst, we recognized a proportional relationship between both concentrations as shown in the next TABLE 1.

TABLE 1

| Concentration of cumene hydroperoxide in feed (weight by %) | Concentration of metal in solution produced (concentrated 200 times) (weight by ppm) Pd(0.3%)/γ-alumina catalyst |
|---|---|
| 2.0 | 7 |
| 4.0 | 14 |
| 8.3 | 32 |
| 16.1 | 46 |

Test liquids were passed at 60° C., and at a LHSV of 6/hour.

That is, as not insignificant quantities of Pd were eluted with aromatic hydroperoxide, the use of a Pd catalyst results in the problem of the inevitable deactivation of the catalyst.

When using a supported Ni catalyst, the catalyst has a disadvantage in spite of having a capacity to reduce aromatic hydroperoxide with hydrogen, of giving a low yield of the desired aromatic alcohols because of many side-reactions (refer to COMPARATIVE EXAMPLE 3 below).

It is an object of the present invention, therefore, to provide a method improved with respect to the catalysts of producing aromatic alcohols wherein no problems such as stated above will occur.

SUMMARY OF THE INVENTION

This invention in outline, relates to a method of producing aromatic alcohols, that is, a method of manufacturing aromatic alcohols by reducing aromatic hydroperoxides with hydrogen in liquid phase which comprises using a Pt catalyst exclusively or using both a catalyst containing Pt and at least one element selected from the group consisting of Pb, Sn, Cu, As, Sb, In, Se and Bi in a fixed bed reactor.

The present inventors, as a result of earnest investigations conducted to overcome said problems, have found that by using a Pt catalyst in a fixed bed reactor in a method of reducing aromatic hydroperoxides with hydrogen in liquid phase, the catalyst will not be deactivated, but rather will achieve high and stable activity even during long periods of use.

Also even though a liquid containing aromatic hydroperoxide was passed over a supported Pt catalyst in accordance with the conditions in TABLE 1, the Pt concentration (after 200-fold concentration) of &he produced liquid did not exceed the limit of detection (1 wt.ppm) and no Pt was found in the production liquid, and it was confirmed that the elution of Pt due to aromatic hydroperoxide hardly occured when a Pt catalyst was used, to complete the present invention.

However, even though the use of a Pt catalyst in a fixed bed reactor may stabilize higher activity, it was determined that as far as slight amounts of impurities were concerned, a part of the produced aromatic alcohol was further converted by aromatic ring hydrogenation to alcohol having a cyclohexane ring (refer to EXAMPLE 12 below). The quantity of this product obtained by aromatic ring hydrogenation is very small, but the boiling point thereof is very near to that of the aromatic alcohol making said product difficult to be removed, resulting in the problem of lowered product purity. Therefore, it is required to develop a catalyst which has long stable hydrogenation activity with less aromatic ring hydrogenation, when producing aromatic alcohols by reducing aromatic hydroperoxides.

The present inventors, for solving said problem, have earnestly conducted investigations and as a result, found that a stable higher activity can be obtained by use of said combined catalyst without accompanying aromatic ring hydrogenation.

DETAILED DESCRIPTION OF THE INVENTION

The present invention will be concretely illustrated below.

(Aromatic hydroperoxides)

As examples of aromatic hydroperoxides to be subjected to the hydrogenation reaction in this invention, alpha phenylethyl hydroperoxide, cumene hydroperoxide, cymene hydroperoxide, o,m- or o,p-diisopropylbenzene monohydroperoxide, o,m- or o,p-diisopropylbenzene dihydroperoxide, isopropylnaphthalene hydroperoxide, etc., and compositions which contain at least one member selected from the group consisting thereof can be given.

(Hydrogen)

The amount of hydrogen to be fed to the hydrogenation reaction system in this invention is 1-50 times as much as the amount theoretically required, preferably 1-30 times and most preferably 1-20 times. Excess feeding of hydrogen causes loss thereof, and requires an undue scale of equipment in recovery and circulating systems, and sometimes gives rise to unnecessary side-reactions.

(Catalyst)

The catalyst components used in the process of producing aromatic alcohols according to this invention are usually supported on suitable carriers. The Pt metal supporting ratios thereof, in regardless of using Pt only or using Pt combined catalysts, are generally 0.01-5 wt. %, preferably 0.03-3 wt. %, wherein the ratio of the elements other than Pt is usually 0.001-3 wt. %, preferably 0.005-2 wt. %.

As for the carriers, heat-resistant inorganic compounds, for example, synthetic gels such as alumina, silica, etc., or natural inorganic carriers such as diatomaceous earth, porous clay, carbon, etc. can be given.

(Reaction mode)

As for the reaction modes in the process of producing aromatic alcohols according to this invention, as shown in Japanese patent Laid-open No.73709/1979, batch process, continuous process or any other suitable process which is well known as a hydrogenation method for organic peroxide can be embodied. However, when a catalyst is employed in a form of suspended bed, a catalyst removal process is needed, making its apparatus complicated: therefore, a fixed bed is preferable. In a fixed bed, when an upflow is used, the catalyst is liable to become fluidized to cause deactivation; therefore, a downflow is more preferable.

As for solvents used for diluting the aromatic hydroperoxides in the method of producing aromatic alcohol according to this invention, any solvent which is capable of dissolving aromatic hydroperoxides along with the products obtained therefrom can be used, and for example, aliphatic hydrocarbons, aromatic hydrocarbons and aromatic alcohols can be given. For instance, in a process of manufacturing cumene hydroperoxide, cumene is present in said process as a solvent, and it can be used as a solvent as it is in a hydrogenation of cumene hydroperoxide in the process of the present invention. In addition it is also a preferable method to recycle cumyl alcohol as shown in a following formula, which is obtained by the hydrogenation of cumene hydroperoxide, to be used as a solvent.

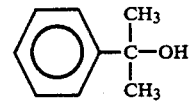

(Concentration of aromatic hydroperoxide)

In the hydrogenation reaction using a catalyst in the process of producing aromatic alcohols according to this invention, it is desirable to control the concentration of aromatic hydroperoxide in the feed liquid supplied to the reactor to at most 25 wt. %. preferably 0.01-15wt, and most preferably 0.1-10 wt. %. When said concentration is more than 25 wt. %, a considerable amount of heat is evolved, causing some problems such as hard control of reaction temperature, depression of high activity, formation of side reactions, etc.

(Reaction temperature)

The hydrogenation reaction, in the method of producing aromatic alcohols according to this invention, is usually conducted in a temperature range of 20°-120° C., preferably 30 -120° C., and most preferably 40°-20° C. Too high a reaction temperature is not desirable, because side reactions such as a decomposition reaction of the aromatic hydroperoxide itself or the like will violently take place. On the other hand too low a reaction temperature will produce problems such as decreased reaction rate, etc.

(Reaction pressure)

The total pressure in the hydrogenation reaction in the method of preparing aromatic alcohols according to this invention, ranges usually from normal pressures to a certain high pressure, preferably from normal pressures to 50 kg/cm²G and most preferably from normal pressures to 30 kg/cm²G. As the hydrogenation reaction proceeds easily, excess reaction pressure just entails excessive apparatus costs for no real effect, and causes problems such as subsequent hydrogenation reaction of the produced liquid and solvent.

EXAMPLES

This invention will be further illustrated in detail with reference to the following examples. In the examples, % is meant to be weight % unless notified to the contrary.

CATALYST PREPARATION EHAMPLE-1

After impregnating a 0.8-1.3% aqueous solution of hydrogen hexachloroplatinate (IV) (hexahydrate) into pellet type γ-alumina with dimensions of 3 mmφ×3 mm, the resultant pellets were dried at 110° C. for 12 hours.

Then, the dried pellets were reduced in a hydrogen stream at 400° C. for 16 hours to obtain a supported Pt catalyst having a composition of Pt(0.3-0.5%)/γ-Al₂O₃.

EXAMPLE-1

A 200 ml autoclave equipped with inlet pipes for raw material and hydrogen and an outlet pipe for liquid products and a basket type of stirrer filled with 0.8 g of catalyst containing 0.3% Pt prepared according to CATALYST PREPARATION EXAMPLE-1 was maintained at 60° C. 1.2L/hour of solution of 3.7% cumenehydroperoxide (hereinafter abbreviated as CHP) in cumene and 12L/hour of hydrogen were fed therein continuously, while the hydrogenation products were continuously collected through the outlet pipe to keep the content in the autoclave at about 80 ml. At this time the hydrogen pressure was kept at 7.5 kg/cm$^2$-G and the stirrer was rotated at 750 rpm. The reaction rate of hydrogenation of CHP after 8 hours from the start of feed is shown in TABLE 2 below.

EXAMPLE-2

The procedure of EXAMPLE-1 was repeated except that the catalyst containing 0.5% of Pt was used and the concentration of CHP and feed rate of hydrogen were increased to 8.0% and 27L/Hours respectively. The results are shown in TABLE 2.

TABLE 2

| EXAMPLE | CHP Concentration [%] | Reaction rate of hydrogenation [mol/kg Pt · hour] |
|---|---|---|
| 1 | 3.7 | 19,000 |
| 2 | 8.0 | 17,800 |

EXAMPLE-3

One liter of catalyst containing 0.3% of Pt prepared according to CATALYST PREPARATION EXAMPLE-1 was charged in a stainless steel tube with an inner diameter of 27.2 mm equipped with a thermowell tube having an outer diameter of 6 mm. keeping the temperature at the entrance of the catalyst layer at 45° C.; 7.2L/hr. of liquid having a composition of 3.5% CHP, 77.0% cumyl alcohol and 19.5% cumene; and 72L/hr. of hydrogen at a pressure of 8 kg/cm$^2$G were continuously fed thereto. The conversion of CHP after 8 hours from the start of feed was 99.9%, and the conversions after 20 and 150 days were 99.7% and 99.9% respectively to obtain stable activity. All the yields of cumyl alcohol based on the amount of CHP fed were 99%.

CATALYST PREPARATION EXAMPLE-2

After impregnating a 0.8% aqueous solution of hydrogen hexachloroplatinate (IV) (hexahydrate) into pellet type γ-alumina with dimensions of 3 mmφ×3 mm, the resultant pellets were dried at 110° C. for 12 hours.

Then, the dried pellets were reduced in a hydrogen stream at 400° C. for 16 hours.

Further impregnating a 0.1% aqueous solution of lead nitrate into the reduced Pt catalyst and after drying it at 110° C. for 12 hours it was reduced in a hydrogen stream at 400° C. for 16 hours to obtain a catalyst having a composition of Pt(0.3%)-Pb(0.03%)/γ-Al$_2$O$_3$.

EXAMPLE-4

The procedure of EXAMPLE-1 was repeated except that the catalyst prepared according to CATALYST PREPARATION EXAMPLE-2 and a 3.5% CHP solution in cumene were used. The results are shown in TABLE 3 below.

In addition, the procedure of EXAMPLE-3 was repeated except that the catalyst prepared according to CATALYST PREPARATION EXAMPLE-2 was used. The conversion of CHP and selectivity to cumyl alcohol and 2-cyclohexyl-2-propanol (nuclear hydrogenation product of cumyl alcohol) after 8 hours from the start of feed are shown in TABLE 3 together with other examples.

CATALYST PREPARATION EXAMPLES 3-9

Except for using in place of the aqueous solution of lead nitrate in CATALYST PREPARATION EXAMPLE-2, 0.1–1.0% solutions of stannous chloride (CATALYST PREPARATION EXAMPLE-3), cupric chloride (CATALYST PREPARATION EXAMPLE-4), arsenic trichloride [dioxane solution] (CATALYST PREPARATION EXAMPLE-5), antimony trichloride (CATALYST PREPARATION EXAMPLE-6), indium chloride (CATALYST PREPARATION EXAMPLE-7), selenium monochloride [benzene solution] (CATALYST PREPARATION EXAMPLE-8), and bismuth nitrate (CATALYST PREPARATION EXAMPLE-9) were used to prepare catalysts according to &he method described in CATALYST PREPARATION EXAMPLE-2, comprising 0.3% of PT, 0.3% of Sn and In or 0.03% of Cu, As, Sb, Se and Bi respectively supported on γ-alumina.

EXAMPLE 5-11

The procedure of EXAMPLE-4 was repeated except that the catalysts prepared in CATALYST PREPARATION EXAMPLES 3 through 9 were used. The results are shown in TABLE 3 below.

EXAMPLE-12

The procedure of EXAMPLE-4 was repeated except that the catalyst containing 0.3% Pt prepared according to CATALYST PREPARATION EXAMPLE-1 was used. The results are shown in TABLE 3.

COMPARATIVE EXAMPLE-1

The procedure of EXAMPLE-4 was repeated except that the catalyst of Pt(0.3%)-Ag(0.03%)/γ-alumina prepared according to CATALYST PREPARATION EXAMPLE-2 using silver nitrate in place of lead nitrate was used. The results are shown in TABLE 3.

TABLE 3

| EXAMPLE | Additive element | Autoclave is used Reaction rate of hydrogenation [mol/kg catalyst · hr] | Fixed bed downflow type reactor is used | | |
|---|---|---|---|---|---|
| | | | Convertion of CHP [%] | Selectivity to cumyl alcohol [%] | Selectivity to 2-cyclohexyl-2-propanol [%] |
| EXAMPLE 4 | Pb | 61.8 | 99.9 | 99.0 | 0.34 |
| EXAMPLE 5 | Sn | 58.1 | 99.9 | 99.2 | 0.01 |
| EXAMPLE 6 | Cu | 57.5 | 99.8 | 99.1 | 0.26 |
| EXAMPLE 7 | As | 61.0 | 99.8 | 99.1 | 0.18 |
| EXAMPLE 8 | Sb | 57.7 | 99.9 | 99.2 | 0.02 |
| EXAMPLE 9 | In | 59.5 | 99.9 | 99.2 | 0.02 |
| EXAMPLE 10 | Se | 61.9 | 99.9 | 99.1 | 0.11 |
| EXAMPLE 11 | Bi | 61.3 | 99.8 | 99.0 | 0.24 |

TABLE 3-continued

| | | Autoclave is used | Fixed bed downflow type reactor is used | | |
|---|---|---|---|---|---|
| EXAMPLE | Additive element | Reaction rate of hydrogenation [mol/kg catalyst · hr] | Convertion of CHP [%] | Selectivity to cumyl alcohol [%] | Selectivity to 2-cyclohexyl-2-propanol [%] |
| EXAMPLE 12 | — | 61.6 | 99.8 | 98.7 | 1.04 |
| COMPARATIVE EXAMPLE 1 | Ag | 0.9 | 2.0 | 97.0 | 0.01 |

COMPARATIVE EXAMPLE-2

After impregnation of a 0.6% aqueous solution of palladium chloride into pellet type γ-alumina with dimensions of 3 mmϕ×3 mm, the pellets were dried at 110° C. for 12 hours.

Then, the dried pellets were reduced in a hydrogen stream of 400° C. for 16 hours to obtain a supported Pd catalyst having a composition of Pd (0.3%)/γ0Al$_2$O$_3$.

The procedure of EXAMPLE-3 was repeated except that the Pd catalyst obtained in such a manner was used. The conversions of CHP after 8 hours and 20 days from the start of feed were 99.9% and 100% respectively, and the conversions after 40 and 70 days were 98.8% and 97.1% respectively, catalytic activity significantly decreasing.

COMPARATIVE EXAMPLE-3

The procedure of EXAMPLE 3 was repeated except that the commercially available Ni catalyst [Trade name: Ni-3266E by Harshaw Co.] was used and the Ni catalyst was pretreated in a hydrogen stream at 250° C. for 4 hours prior to feed. The conversion of CHP after 8 hours from the start of feed was 97%, the yield of cumyl alcohol was as low as 81% and by-products as acetophenone, α-methylstyrene, 1-phenylethanol, etc. were found.

As can be understood from the above, the manufacturing methods according to this invention permit stable hydrogenation of aromatic hydroperoxide with a high conversion rate as well as the production of corresponding aromatic alcohol with selectivity.

What is claimed is:

1. A method for producing an alcohol, comprising: reducing an aromatic hydroperoxide selected from the group consisting of α-phenylethyl hydroperoxide, cumene hydroperoxide, cymene hydroperoxide, o,m- or o,p-diisopropylbenzene monohydroperoxide, o,m- or o,p-diisopropylbenzene dihydroperoxide, and isopropylnaphathalene hydroperoxide with hydrogen in a liquid phase at a temperature ranging from 20°-120° C. under a total pressure ranging from atmospheric pressure to 50 kg/cm$^2$G in the presence of a catalyst of Pt or Pt combined with at least one element selected from the group consisting of Pb, Sn, Cu, As, Sb, In, Se and Bi in a fixed bed reactor.

2. The method according to claim 1, wherein the catalyst consists of Pt.

3. The method according to claim 1, wherein the catalyst consists of Pt and Sn.

4. The method according to claim 1, wherein the catalyst consists of Pt and Sb.

5. The method according to claim 1, wherein the catalyst consists of Pt and In.

6. The method according to any one of claim 1 to 5, wherein the catalyst is supported on γ-alumina.

7. The method according to claim 6, wherein 0.01 to 5 weight % of Pt is supported on said γ-alumina support.

8. The method according to claim 6, wherein 0.01 to 5 weight % of Pt and 0.001 to 3 weight % of at least one element selected from the group of consisting of Pb, Sn, Cu, As, Sb, In, Se and Bi are supported on said γ-alumina support.

9. The method according to claim 1, wherein the aromatic hydroperoxide is cumene hydroperoxide.

10. The method according to claim 1, wherein a concentration of the aromatic hydroperoxide in a feed is 0.01 to 15 weight %.

11. The method according to claim 1, wherein the amount of hydrogen present in said reaction ranges from 1–50 times the theoretical amount of hydrogen required.

12. The method according to claim 1, wherein the reaction is conducted in a liquid phase medium of an aliphatic hydrocarbon, an aromatic hydrocarbon or an aromatic alcohol.

13. The method according to claim 10, wherein the concentration of said aromatic hydroperoxide in said feed ranges from 0.1–10 weight %.

14. The method according to claim 1, wherein the reaction temperature ranges from 30°-120° C.

15. The method according to claim 1, wherein said reaction pressure ranges from atmospheric pressure to 30 kg/cm$^2$G.

* * * * *